United States Patent
Ni et al.

(10) Patent No.: US 10,845,301 B2
(45) Date of Patent: Nov. 24, 2020

(54) MULTI-ROTOR WING UNMANNED AERIAL VEHICLE PLATFORM BASED CROP GROWTH MONITORING METHOD AND DEVICE

(71) Applicant: NANJING AGRICULTURAL UNIVERSITY, Nanjing (CN)

(72) Inventors: Jun Ni, Nanjing (CN); Lili Yao, Nanjing (CN); Yan Zhu, Nanjing (CN); Weixing Cao, Nanjing (CN); Xia Yao, Nanjing (CN); Yongchao Tian, Nanjing (CN); Fang Liu, Nanjing (CN); Fangrong Pang, Nanjing (CN)

(73) Assignee: NANJING AGRICULTURAL UNIVERSITY, Nanjing (CN)

( * ) Notice: Subject to any disclaimer, the term of this patent is extended or adjusted under 35 U.S.C. 154(b) by 246 days.

(21) Appl. No.: 16/066,675

(22) PCT Filed: Dec. 27, 2016

(86) PCT No.: PCT/CN2016/112369
§ 371 (c)(1),
(2) Date: Jun. 28, 2018

(87) PCT Pub. No.: WO2017/114387
PCT Pub. Date: Jul. 6, 2017

(65) Prior Publication Data
US 2019/0011355 A1    Jan. 10, 2019

(30) Foreign Application Priority Data

Dec. 28, 2015   (CN) .......................... 2015 1 1008339

(51) Int. Cl.
*G01N 21/31*   (2006.01)
*B64C 39/02*   (2006.01)
(Continued)

(52) U.S. Cl.
CPC .......... *G01N 21/314* (2013.01); *B64C 39/024* (2013.01); *G01N 21/31* (2013.01);
(Continued)

(58) Field of Classification Search
CPC ...... G01N 21/314; G01N 21/31; G01N 21/25; G01N 2201/0214; G01N 2021/8466;
(Continued)

(56) References Cited

FOREIGN PATENT DOCUMENTS

| CN | 102102988 A | 6/2011 |
|---|---|---|
| CN | 102768186 A | 11/2012 |

(Continued)

OTHER PUBLICATIONS

Xiang et al., Development of a Low-Cost Agricultural Remote Sensing System Based on an Autonomous Unmanned Aerial Vehicle (UAV), Published Online Jan. 11, 2011, Biosystems Engineering, vol. 108, pp. 174-190 (Year: 2011).*

(Continued)

*Primary Examiner* — Toan M Le
(74) *Attorney, Agent, or Firm* — Bayramoglu Law Offices LLC (57) ABSTRACT

A crop growth monitoring device based on multi-rotor unmanned aerial vehicle platform includes a multi-rotor unmanned aerial vehicle, a payload and a ground receiver; the payload part includes a multispectral crop growth sensor module, a signal amplification module, a controller module, a wireless data transmission module, and a power module for power supply and a power supply control module, which are connected in sequence; further comprising a gimbal. The crop growth monitoring device based on the multi-rotor unmanned aerial vehicle platform overcomes the influence on measurement caused by the down-wash flow field of the unmanned aerial vehicle, and can transmit the measured data to the ground receiver in real time for online analysis and (Continued)

processing, realizing continuous, real-time, convenient and large-scope acquisition of crop growth information.

8 Claims, 7 Drawing Sheets (51) Int. Cl.
G01N 33/00 (2006.01)
G01N 21/84 (2006.01)

(52) U.S. Cl.
CPC .... *G01N 33/0098* (2013.01); *B64C 2201/024* (2013.01); *B64C 2201/12* (2013.01); *G01N 2021/317* (2013.01); *G01N 2021/3181* (2013.01); *G01N 2021/8466* (2013.01); *G01N 2201/0214* (2013.01)

(58) Field of Classification Search
CPC .............. G01N 33/0098; B64C 39/024; B64C 2201/024; B64C 2201/12; B64C 2201/123
See application file for complete search history.

(56) References Cited

FOREIGN PATENT DOCUMENTS

| | | |
|---|---|---|
| CN | 103175789 A | 6/2013 |
| CN | 103425102 A | 12/2013 |
| CN | 103488179 A | 1/2014 |
| CN | 203512034 U | 4/2014 |
| CN | 103885454 A | 6/2014 |
| CN | 104035412 A | 9/2014 |
| CN | 104050649 A | 9/2014 |
| CN | 204514798 U | 7/2015 |
| CN | 204536909 U | 8/2015 |
| CN | 104881042 A | 9/2015 |
| CN | 105025262 A | 11/2015 |
| CN | 105510242 A | 4/2016 |
| EP | 1873574 A2 | 1/2008 |

OTHER PUBLICATIONS

Vega et al., Multi-Temporal Image Using an Unmanned Aerial Vehicle for Monitoring a Sunflower Crop, Published Online Feb. 18, 2015, Biosystems Engineering, vol. 132, pp. 19-27 (Year: 2015).*

Xia Yao et al; Wheat Nitrogen Nutrition and Growth Monitoring Based on Remote Sensing of Unmanned Aerial Vehicles; 2014 China Crop Society Academic Annual Conference Abstracts; p. 193.

* cited by examiner

MULTI-ROTOR WING UNMANNED AERIAL VEHICLE PLATFORM BASED CROP GROWTH MONITORING METHOD AND DEVICE

CROSS REFERENCE TO RELATED APPLICATIONS

This application is the national phase entry of International Application No. PCT/CN2016/112369, filed on Dec. 27, 2016, which is based upon and claims priority to Chinese Patent Application No. 201511008339.7, filed on Dec. 28, 2015, the entire contents of which are incorporated herein by reference.

TECHNICAL FIELD

The present invention relates to a crop growth monitoring method and device based on a multi-rotor unmanned aerial vehicle platform, and relates to the field of precision agriculture, specifically, to crop growth monitoring and diagnosis, and in particular, to large-region, high-throughput, continuous, rapid, and real-time monitoring and diagnosis of crop growth information based on an unmanned aerial vehicle platform.

BACKGROUND

Real-time, non-destructive, and high-throughput acquisition of crop growth information is the prerequisite for precise management of crop production. In traditional crop production management, accurate quantitative knowledge of the crop growth status is often lacking; or despite quantitative analysis of crop growth indexes, destructive sampling and chemical analysis is relied on, and due to its poor time-effectiveness, excessive application of fertilizers (especially nitrogen fertilizers or insufficient application of fertilizers (for example, some trace elements) generally exists in production, which easily causes increase of production costs, environmental pollution, and decrease of sustainable land production capability. In recent years, non-destructive monitoring technologies for recognizing object features based on reflection spectra have developed rapidly, making it possible to acquire the plant growth status and plant biochemical components efficiently, precisely, and non-destructively in real time, so as to provide new ways and methods for non-destructive monitoring and diagnosis of crop growth. The patent ZL201210214137.8 invents a multispectral crop growth sensor based on the crop growth spectra monitoring theory, and discloses a portable growth monitoring diagnostic apparatus capable of acquiring crop growth information non-destructively in real time. The apparatus needs to be used in an environment with clear weather without wind or clouds and with a relatively static crop canopy, the working height should be set to 1-1.2 meters above the canopy, and the apparatus can be used in a convenient and flexible way with high precision. However, the single-point measurement technology has a limited monitoring range, high labor intensity, and high labor costs, and causes great human destruction to crops during the field operation. Multi-rotor unmanned aerial vehicles have such characteristics as simple and efficient operation, flexible hovering, and high terrain adaptability, and as a result, play an increasingly prominent role and have increasingly wide application in crop seedling growth monitoring, artificial pollination, and plant protection against diseases.

In the existing art, crop growth monitoring based on multi-rotor unmanned aerial vehicle platform is always combined with multispectral or hyperspectral cameras. Specifically, the camera is loaded on a gimbal of an UAV for obtaining crop images. Then, these acquired photos are corrected offline and spliced using special remote-sensing analysis software to interpret crop growth information. The process is complex, requires remote sensing professionals, and is mostly applied in scientific research; furthermore, the interpreted crop growth information lags and cannot be directly applied in agricultural production, and various imaging spectrometer payloads that are carried have high costs and cannot be popularized in agricultural production. When the unmanned aerial vehicle carries a multispectral sensor for test, limited by the effective test height of the sensor, a high-intensity and high-density air flow field is produced when rotors hover at low altitude and is directly applied to the crop canopy, causing the canopy to be in a "nonstationary" random dynamic change and the sensor to be unable to effectively capture a canopy reflectance spectra; besides, under the action of the down-wash flow field of the unmanned aerial vehicle, specular reflection of leaves in the canopy is more prominent, while the premise of the crop growth spectra monitoring theory is to assume that the crop canopy shows Lambertian properties, so simply applying the crop growth spectroscopy sensor and growth monitoring model to the unmanned aerial vehicle platform still has a lot of problems.

SUMMARY

The technical problem to be solved by the present invention is to provide a crop growth monitoring method and device applied to a multi-rotor unmanned aerial vehicle platform in view of the deficiency in the Background. The device overcomes the influence on measurement caused by a down-wash flow field of an unmanned aerial vehicle, and can transmit measured data to a ground receiver in real time for online analysis and processing, realizing continuous, real-time, high-throughput, and large-scope acquisition of crop growth information.

A crop growth monitoring method based on a multi-rotor unmanned aerial vehicle platform includes the following steps:

step 1. fixing a multispectral crop growth sensor on a gimbal support;

step 2. operating a flight controller, so that an unmanned aerial vehicle hovers at a height h over a crop canopy and the multispectral crop growth sensor acquires reflectance spectra of the crop canopy in real time;

step 3. operating an "ON" button of a ground receiver, so that the ground receiver is initialized, a communicating LED module starts wireless connection with a payload, a red light LED flickers at a frequency of 1 KHz, and the red light LED is turned on after successful connection;

step 4. operating a "MEASURE" button of the ground receiver, so that a blue light LED flickers at a frequency of 1 KHz, data enters a data processing module through a wireless receiving module, and a liquid crystal display (LCD) screen displays canopy NDVI values and RVI values in real time, and operating the "MEASURE" button again, so that the NDVI value and the RVI value are locked on the LCD screen;

step 5. operating a "MONITOR" button of the ground receiver to invoke a crop growth monitoring model, so that the LCD screen displays a leaf nitrogen content, a leaf nitrogen accumulation, a leaf area index, and a leaf dry weight index; and step 6. operating a "DIAGNOSIS" button of the ground receiver to invoke a crop growth diagnosis model, so that the LCD screen displays a nitrogen fertilizer deficiency extent and a regulation amount.

Preferably, the crop growth monitoring method based on a multi-rotor unmanned aerial vehicle platform further includes step 7: operating a "RESET" button of the ground receiver, so that the ground receiver returns to an initialized state. Preferably, the data entering a data processing module through a wireless receiving module is specifically: data of the crop canopy reflectance spectra enters the data processing module through the wireless receiving module, and data of sunlight incidence spectra enters the data processing module through an analog I/O interface.

Preferably, the data are coupled into the invoked crop growth monitoring model.

Preferably, a position for the fixing a multispectral crop growth sensor on a gimbal support in step 1 is determined according to the following method:

1) three-dimensional modeling of curved surfaces of unmanned aerial vehicle rotors and fuselage:

for different types of multi-rotor unmanned aerial vehicles, digitizing rotor and fuselage entities by means of three-dimensional scanning to obtain spatial coordinate data of the curved surfaces of the rotors and the fuselage, then, performing reverse modeling of the rotors and the fuselage, and finally, assembling the rotors and the fuselage according to an entity graph;

2) entity grid partitioning and data solution for the unmanned aerial vehicle:

establishing a fluid motion control equation set according to an operating state of the unmanned aerial vehicle and a flowing state of down-wash air flows, and determining an initial condition and a boundary condition; partitioning stationary and rotating regions, determining a junction, and performing region discretization and performing grid partitioning on the discretized regions;

3) numerical calculation and analysis of a flow field:

performing numerical calculation on a flow field produced by the hovering unmanned aerial vehicle, so as to acquire a basic form of a rotor-induced velocity field, as well as distributions of velocity field and pressure field at different height planes;

4) determination of the position for fixing the multispectral crop growth sensor:

measuring the height h at which the unmanned aerial vehicle hovers over the crop canopy, determining, according to a distribution range of the air-flow velocity field at the canopy surface, a length of the gimbal support to be greater than a diameter of an air-flow velocity field at the canopy surface, mounting the multispectral crop growth sensor on one end of the support, and mounting a counterweight of the same weight as the sensor, on the other end of the support, where the multispectral sensor measures a canopy target beyond the air-flow velocity field.

Furthermore, the length of the gimbal support is determined to be greater than a sum of the diameter of the air-flow velocity field at the canopy surface.

A crop growth monitoring device based on a multi-rotor unmanned aerial vehicle platform includes a multi-rotor unmanned aerial vehicle, a payload, and a ground receiver.

The payload part includes a multispectral crop growth sensor module 106 a signal amplification module 105, a controller module 103, a wireless data transmission module 104, and a power module 101 for power supply and a power supply control module 102, which are connected in sequence; the payload part further includes a gimbal, where the power module 101 supplies power to the power supply control module 102; the power supply control module 102 is separately connected to the multispectral crop growth sensor module 106, the signal amplification module 105, the controller module 103, and the wireless data transmission module 104; the gimbal includes a gimbal support 108, a fixing buckle 109, and a sensor counterweight 107; the multispectral crop growth sensor module 106, the signal amplification module 105, the controller module 103, the wireless data transmission module 104, the power module 101, and the power supply control module 102 are integrated and fixed on one end of the gimbal support 108; the sensor counterweight 107 is fixed on the other end of the gimbal support 108; the gimbal is fastened to the unmanned aerial vehicle by means of the fixing buckle 109.

The ground receiver part includes a wireless data receiving module 214, a signal amplification module 205, a data processing module 212, a communicating LED module 211, a button control module 213, an LCD screen display module 210, and a power module 201 for power supply and a power supply control module 202, which are connected in sequence; the ground receiver part further includes a ground receiver housing, where the power module 201 supplies power to the power supply control module 202; the power supply control module 202 is separately connected to the wireless data receiving module 214, the signal amplification module 205, the data processing module 212, the communicating LED module 211, the button control module 213, and the LCD screen display module 210; the power module 201, the power supply control module 202, the wireless data receiving module 214, the signal amplification module 205, the data processing module 212, the communicating LED module 211, the button control module 213, and the LCD screen display module 210 are encapsulated in the ground receiver housing.

As a further optimized solution of the crop growth monitoring device based on a multi-rotor unmanned aerial vehicle platform, a position where the multispectral crop growth sensor is mounted on the gimbal support is determined from a horizontal distribution of a down-wash flow field produced by the hovering multi-rotor unmanned aerial vehicle and an angular range of a field of view of the multispectral growth sensor.

As a further optimized solution of the crop growth monitoring device based on a multi-rotor unmanned aerial vehicle platform in the present invention, the crop growth monitoring device based on a multi-rotor unmanned aerial vehicle platform according to claim 5, where the communicating LED module includes a blue light LED and a red light LED.

As a further optimized solution of the crop growth monitoring device based on a multi-rotor unmanned aerial vehicle platform in the present invention, the button module includes "ON" "OFF", "MEASURE", "MONITOR", and "DIAGNOSIS", and may further include a "RESET" control button. The button module employs a dual-button circuit and a button anti-shake circuit, and in order to achieve a desirable anti-shake effect, the button anti-shake circuit utilizes an RC integral circuit to achieve clutter removal and waveform correction.

As a further optimized solution of the crop growth monitoring device based on a multi-rotor unmanned aerial vehicle platform in the present invention, the wireless data transmission module and the wireless data receiving module have a frequency band at 780 MHz.

As a further optimized solution of the crop growth monitoring device based on a multi-rotor unmanned aerial vehicle platform in the present invention, the power supply control module includes a trigger, a buck circuit, a voltage stabilizing circuit, and a decoupling circuit, where the trigger is connected to the buck circuit, the voltage stabilizing circuit, and the decoupling circuit in sequence.

By means of the aforementioned technical solutions, the present invention has the following beneficial effects as compared with the existing art:

1. The crop growth monitoring device based on a multi-rotor unmanned aerial vehicle platform in the present invention reduces effective costs of the spectra monitoring apparatus of the unmanned aerial vehicle.

2. The crop growth monitoring device based on a multi-rotor unmanned aerial vehicle platform in the present invention overcomes the influence on measurement caused by the down-wash flow field of the unmanned aerial vehicle.

3. The crop growth monitoring device based on a multi-rotor unmanned aerial vehicle platform in the present invention can transmit measured data to the ground receiver in real time for online analysis and processing, realizing continuous, real-time, high-throughput, and large-scope acquisition of crop growth information.

4. The crop growth monitoring device based on a multi-rotor unmanned aerial vehicle platform in the present invention can couple multiple crop growth diagnosis models at the same time, and perform inversion to obtain multiple agricultural growth parameters such as a leaf nitrogen content, a leaf nitrogen accumulation, a leaf area index, and a leaf dry weight index.

DETAILED DESCRIPTION OF THE EMBODIMENTS

The specific implementations of the present invention are described in further detail below with reference to the drawings and embodiments.

The following embodiments are used for illustrating the present invention, rather than limiting the scope of the present invention.

Figure 1:
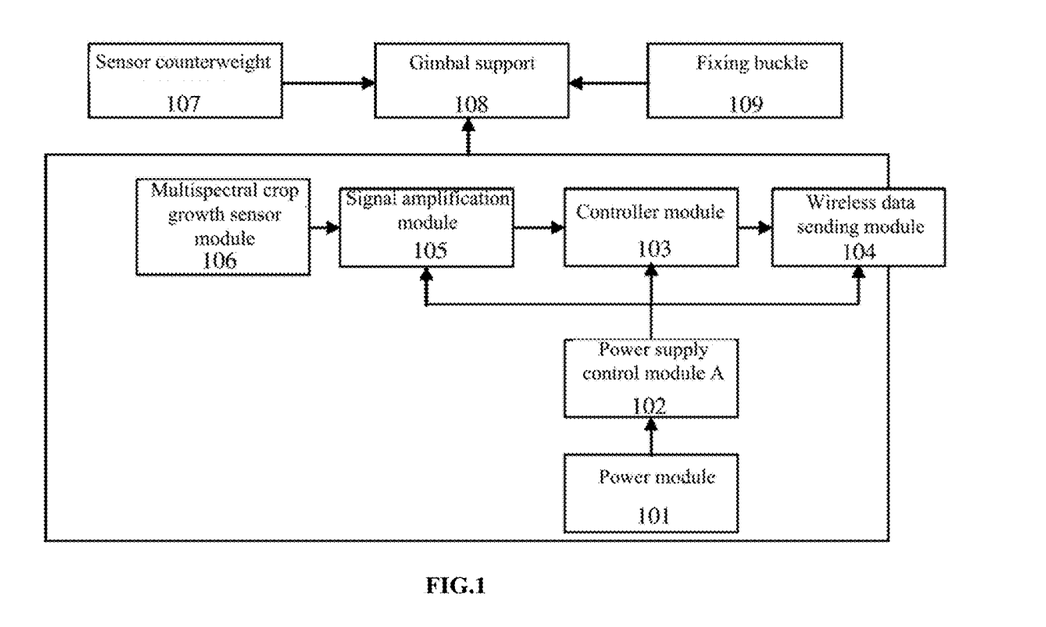
FIG. 1 is a schematic structural diagram of a payload part.

Referring to FIG. 1, a crop growth monitoring device based on a multi-rotor unmanned aerial vehicle platform is illustrated, where a payload part includes a multispectral crop growth sensor module 106, a signal amplification module 105 a controller module 103, a wireless data transmission module 104, and a power module 101 for power supply and a power supply control module 102, which are connected in sequence; the payload part further includes a gimbal. The power module 101 supplies power to the power supply control module 102; the power supply control module 102 is separately connected to the multispectral crop growth sensor module, the signal amplification module 105, the controller module 103, and the wireless data transmission module 104; the gimbal includes a gimbal support 108, a fixing buckle 109, and a sensor counterweight 107; the multispectral crop growth sensor module 106, the signal amplification module 105, the controller module 103, the wireless data transmission module 104, the power module 101, and the power supply control module 102 are integrated and fixed on one end of the gimbal support 108; the sensor counterweight 107 is fixed on the other end of the gimbal support 108; the gimbal is fastened to an aerial vehicle by means of the fixing buckle 109.

Figure 2:
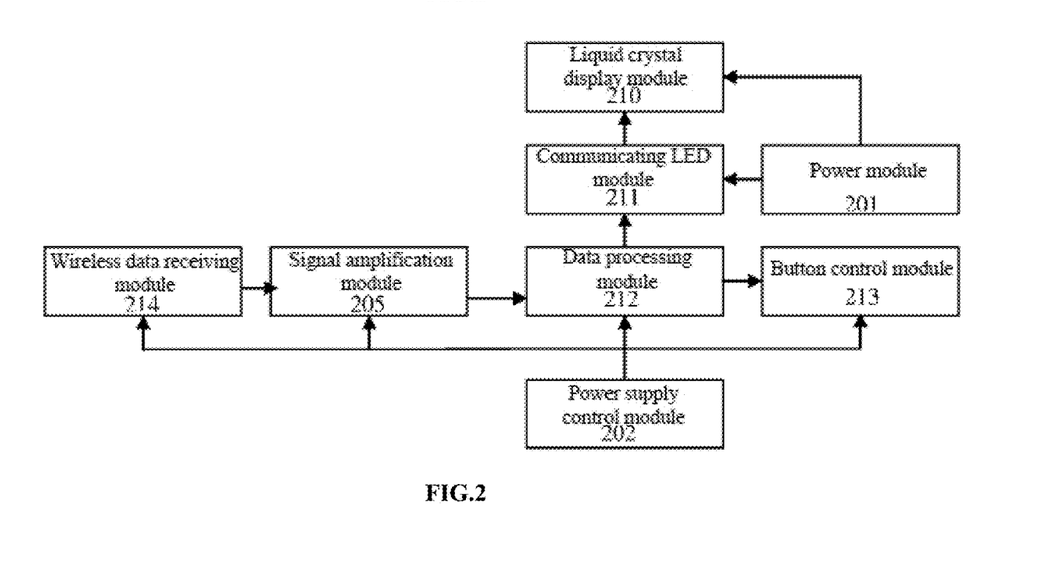
FIG. 2 is a schematic structural diagram of a ground receiver part.

Referring to FIG. 2, a crop growth monitoring device based on a multi-rotor unmanned aerial vehicle platform is illustrated, where a ground receiver part includes a wireless data receiving module 214, a signal amplification module 205, a data processing module 212, a communicating LED module 211, a button control module 213, an LCD screen display module 210, and a power module 201 for power supply and a power supply control module 202, which are connected in sequence; the ground receiver part further includes a ground receiver housing. The power module 201 supplies power to the power supply control module 202; the power supply control module 202 is separately connected to the wireless data receiving module 214, the signal amplification module 205, the data processing module 212, the communicating LED module 211, the button control module 213, and the LCD screen display module 210. The power module 201, the power supply control module 202, the wireless data receiving module 214, the amplification module 205, the data processing module 212, the communicating LED module 211, the button control module 213, and the LCD screen display module 210 are encapsulated in the ground receiver housing.

Figure 3A:
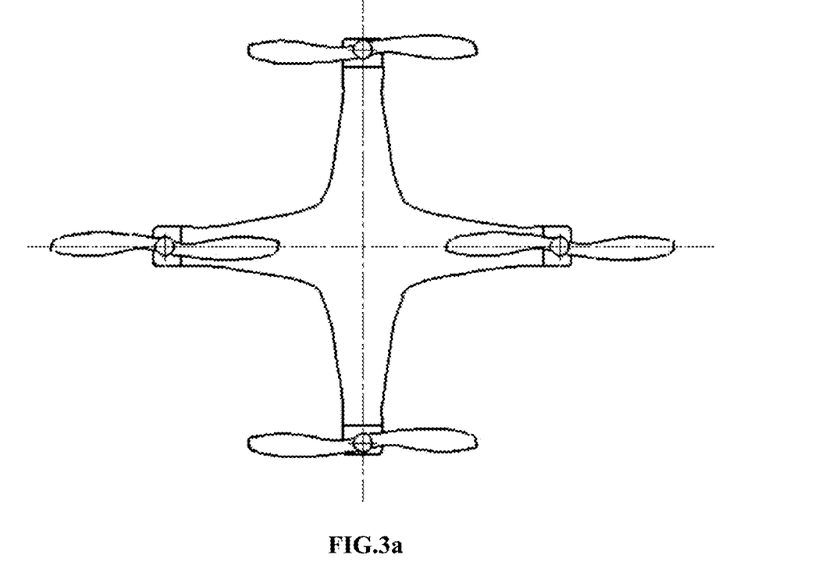
FIG. 3a is a schematic planar structural view of rotors and a fuselage of a quadrotor unmanned aerial vehicle.
Figure 3B:
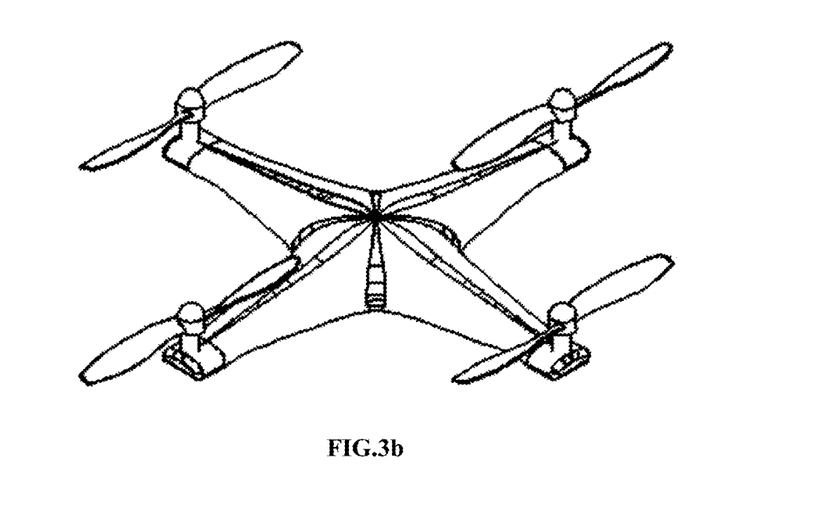
FIG. 3b is a schematic three-dimensional structural view of the rotors and the fuselage of the quadrotor unmanned aerial vehicle.

Referring to FIG. 3, a crop growth monitoring method based on a multi-rotor unmanned aerial vehicle platform is illustrated, where a phantom quadrotor unmanned aerial vehicle from DJI-Innovations is used as an example, rotor and fuselage entities are digitized by means of three-dimensional scanning to obtain spatial coordinate data of curved surfaces of the rotors and the fuselage, positioning lines and surfaces are found in reverse engineering, sections and section lines are drawn and aligned with the x axis, y axis, and z axis, entity modeling of the rotors and the fuselage is completed, and the rotors and the fuselage are assembled.

Figure 4A:
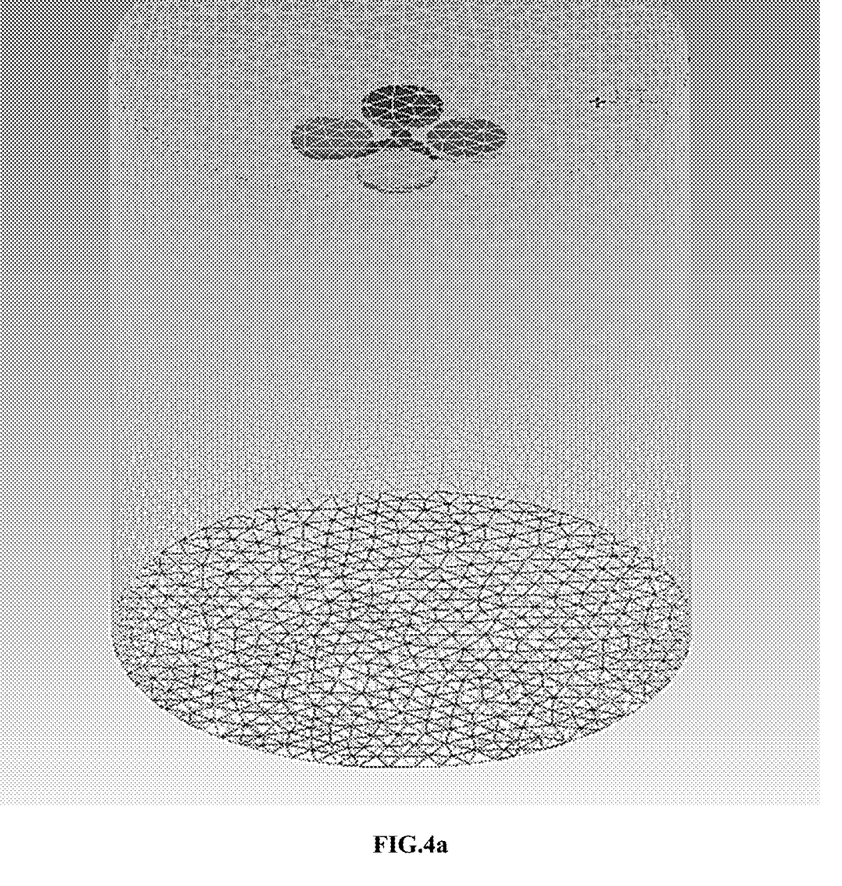
FIG. 4a is a schematic view illustrating grid partitioning of a stationary region of the quadrotor unmanned aerial vehicle.
Figure 4B:
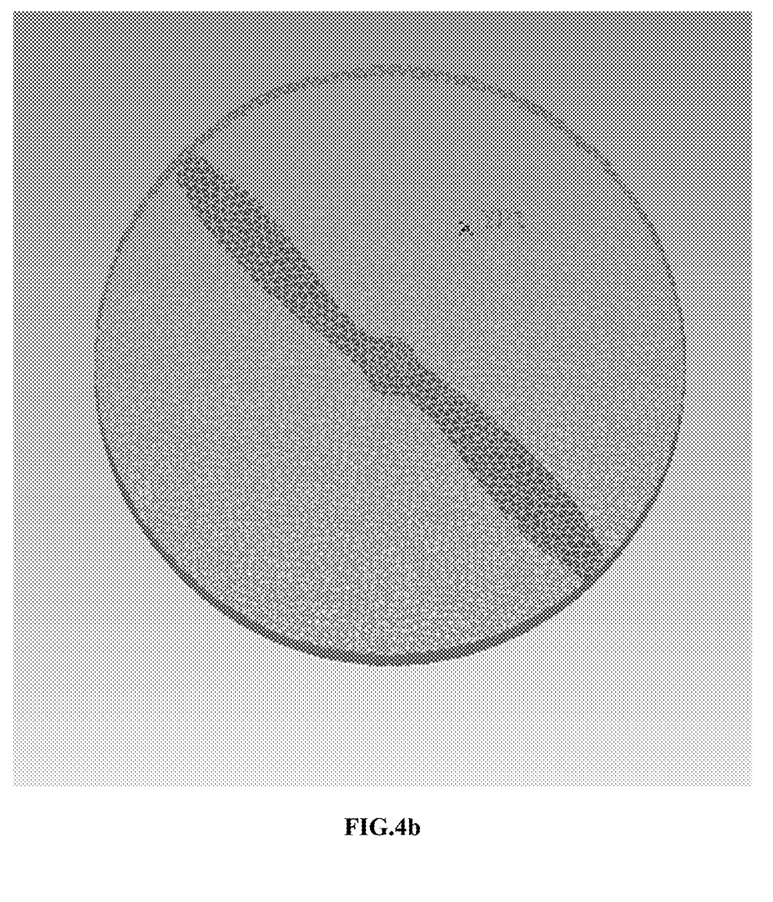
FIG. 4b is a schematic view illustrating grid partitioning of a rotating region of the quadrotor unmanned aerial vehicle.

Referring to FIG. 4, a crop growth monitoring method based on a multi-rotor unmanned aerial vehicle platform is illustrated, where a mass conservation equation, a momentum conservation equation, and an energy conservation equation for down-wash air flow motion are established according to critical dimensions of rotors of the phantom quadrotor unmanned aerial vehicle, namely, a rotor radius of 103.5 mm, an axial length of 390 mm, and a rotor gap of 250 mm, a rated rotor operating speed of 960 r/min, and a height at which the unmanned aerial vehicle operates over the canopy. An adiabatic wall and an impervious boundary are used as an object plane boundary condition, a pressure far field boundary is used as a far field boundary condition, a calculation region is divided into a rotating region including the 4 rotors and a stationary region including the fuselage and an air flow field, the stationary region has a diameter of 1200 mm and a height of 1850 mm; the rotating region has a diameter of 275 mm and a height of 18 mm, where the rotors are at a distance of 1500 mm from the bottom. Body-fitted grids are used to perform unstructured grid partitioning on the stationary region and the rotating region, where the number of grids of the stationary region is 875695, the number of grids of the rotating region is 603564, and the rotor grids and the fuselage grids are joined by means of an interface.

Figure 5:
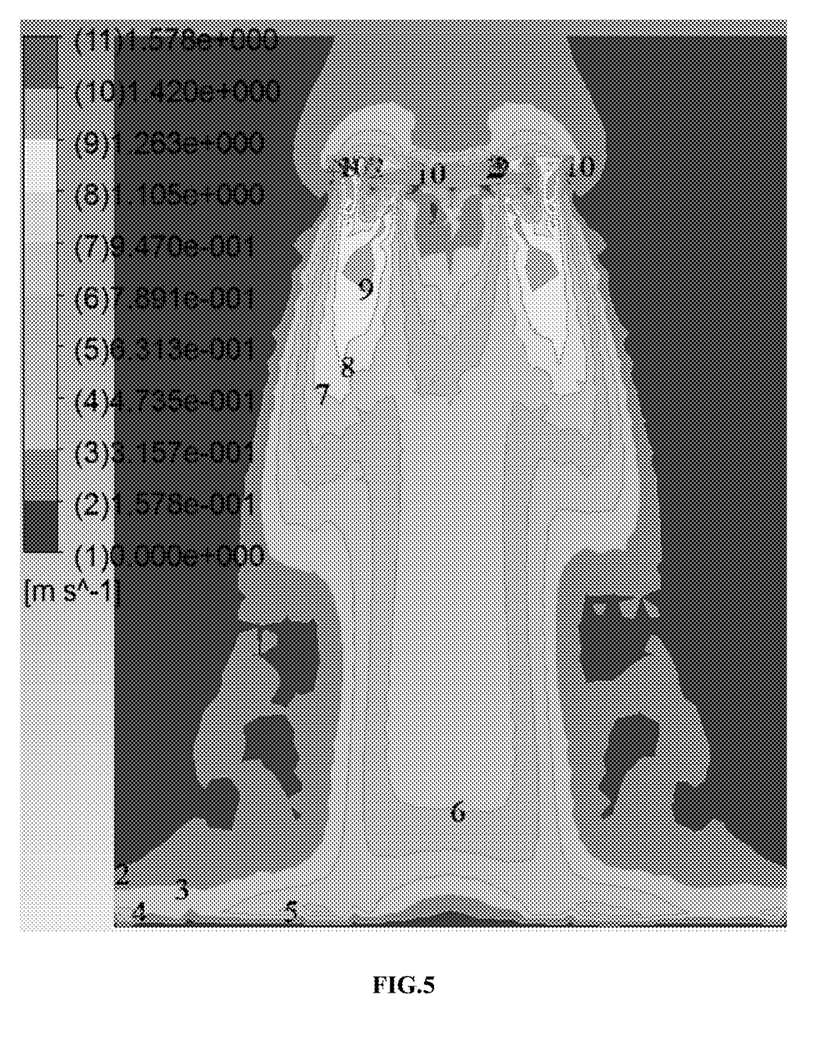
FIG. 5 is a velocity cloud diagram of an axial section 1.3 m under the rotors of the quadrotor unmanned aerial vehicle.
Figure 6:
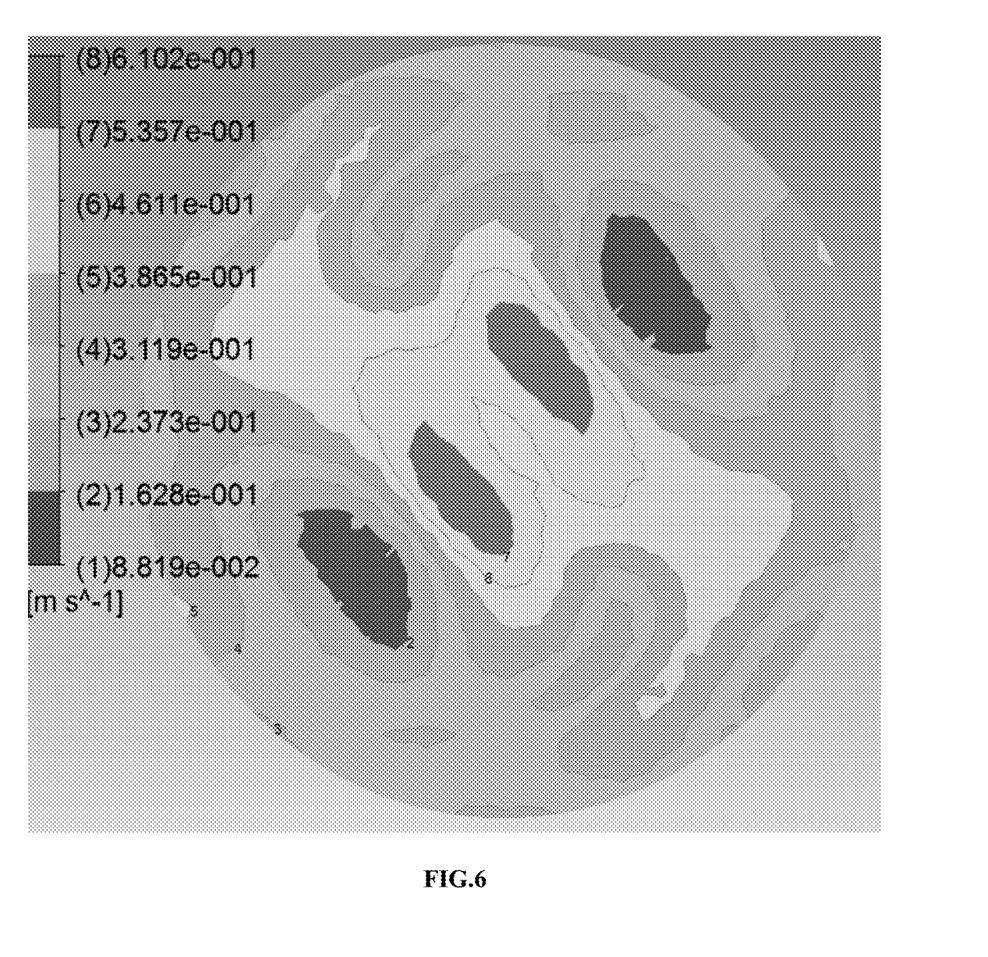
FIG. 6 is a velocity cloud diagram of a cross section x-y 1.3 in under the rotors of the quadrotor unmanned aerial vehicle.

Referring to FIG. 5 and FIG. 6, a crop growth monitoring method based on a multi-rotor unmanned aerial vehicle platform is illustrated, where according to said set parameters, numerical calculation is performed on the flow field produced by the hovering phantom quadrotor unmanned aerial vehicle, and a postprocessing module built in CFX is used for visualization. As can be seen from the axial section velocity cloud diagram, on the one hand, the air flow is flung out by the rotors rotating at a high speed, and on the other hand, it is compressed by the rotors, thus forming a high-speed flowing region near the rotors with large velocity values and strong axial components. As can be seen from the cross section velocity cloud diagram, the flow field has high central velocity and progressively decreased peripheral velocity; the velocity field induced below the rotors is symmetrically distributed with respect to the central axis, and the farther from the central axis, the smaller the velocity gradient and velocity values. Due to the influence caused by the rotating direction of the rotating axis, air flows in the lower part tend to be concentrated on two sides, and as the height continuously decreases, the velocity in the z direction gradually decreases, and the action area of the air flows becomes larger and larger.

Figure 7A:
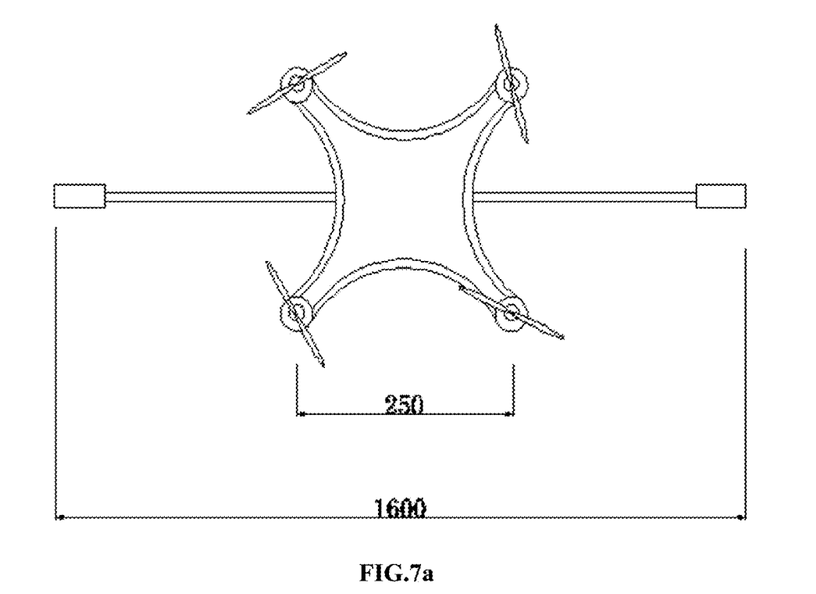
FIG. 7a is a schematic top structural view of a gimbal support of the quadrotor unmanned aerial vehicle.
Figure 7B:
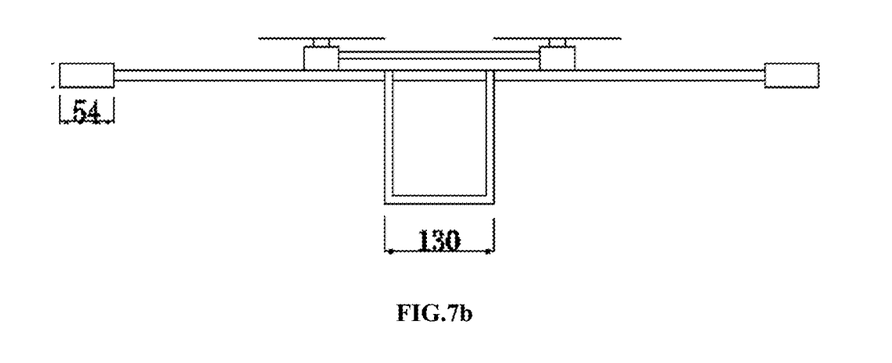
FIG. 7b is a schematic side structural view of the gimbal support of the quadrotor unmanned aerial vehicle.

Referring to FIG. 7, a crop growth monitoring method based on a multi-rotor unmanned aerial vehicle platform is illustrated, where the phantom quadrotor unmanned aerial vehicle operates at a height of 1300 mm over the canopy, a canopy measurement point is selected to be at a distance of 800 mm from the center of the velocity field according to the distribution range of an air flow velocity field at the canopy surface, the length of the gimbal support is determined to be 1600 mm, the multispectral crop growth sensor is mounted on one end of the support, and a counterweight of the same weight as the sensor is mounted on the other end of the support.

The above-described embodiments are merely used for describing preferred implementations of the present invention, rather than limiting the concept and scope of the present invention. Various modifications and improvements made by those of ordinary skill in the art to the technical solutions of the present invention without departing from the design concept of the present invention shall fall within the protection scope of the present invention. The inventive technical contents to be protected are disclosed in the claims.

What is claimed is:

1. A crop growth monitoring method based on a multi-rotor unmanned aerial vehicle platform, comprising the following steps:

step 1) fixing a multispectral crop growth sensor on a gimbal support;

step 2) operating a flight controller, so that an unmanned aerial vehicle hovers at a height over a crop canopy, and the multispectral crop growth sensor acquires reflectance spectra of the crop canopy in real time;

step 3) operating an "ON" button of a ground receiver, so that the ground receiver is initialized, a communicating LED module starts wireless connection with a payload, a red light LED flickers at a frequency of 1 KHz, and the red light LED is turned on after successful connection;

step 4) operating a "MEASURE" button of the ground receiver, so that a blue light LED flickers at a frequency of 1 KHz, data enter a data processing module through a wireless receiving module, and a Liquid Crystal Display (LCD) screen displays canopy Normalized Difference Vegetation Index (NDVI) values and Ratio Vegetation Index (RVI) values in real time; operating the "MEASURE" button again, so that the NDVI value and the RVI value are locked on the LCD screen;

step 5) operating a "MONITOR" button of the ground receiver to invoke a crop growth monitoring model, so that the LCD screen displays a leaf nitrogen content, a leaf nitrogen accumulation, a leaf area index, and a leaf dry weight index; and step 6) operating a "DIAGNOSE" button of the ground receiver to invoke a crop growth diagnosis model, so that the LCD screen displays a nitrogen fertilizer deficiency extent and a regulation amount, wherein a position for fixing the multispectral crop growth sensor on the gimbal support in step 1 is determined according to the following method:

1) modeling curved surfaces of rotors and a fuselage of multi-rotor unmanned aerial vehicle in three-dimensional;

for different types of multi-rotor unmanned aerial vehicles, digitizing the rotors and the fuselage by means of three-dimensional scanning to obtain spatial coordinate data of the curved surfaces of the rotors and the fuselage, then, performing reverse modeling of the rotors and the fuselage, and finally, assembling the rotors and the fuselage according to an entity graph;

2) partitioning entity grid of the unmanned aerial vehicle and calculating and analyzing data;

establishing a fluid motion control equation set according to an operating state of the unmanned aerial vehicle and a flowing state of down-wash air flows, and determining an initial condition and a boundary condition; partitioning stationary and rotating regions, determining a junction, and performing region discretization; and performing grid partitioning on a discretized region;

3) calculating and analyzing numerical values of a flow field:

performing numerical calculation on the flow field produced by the unmanned aerial vehicle hovering over the crop canopy, so as to acquire a basic form of a rotor-induced velocity field, as well as distributions of a velocity field and a pressure field at different height planes;

4) determining the position for fixing the multispectral crop growth sensor:

measuring the height at which the unmanned aerial vehicle hovers over the crop canopy, determining, according to a distribution range of the air-flow velocity field at the canopy surface, a length of the gimbal support to be greater than a diameter of an air-flow velocity field at the canopy surface, mounting the multispectral crop growth sensor on a first end of the gimbal support, and mounting a counterweight of the same weight as the sensor on a second end of the gimbal support, wherein a multispectral sensor measures a canopy target beyond the air-flow velocity field.

2. The crop growth monitoring method based on the multi-rotor unmanned aerial vehicle platform according to claim 1, wherein the method further comprises step 7: operating a "RESET" button of the ground receiver, so that the ground receiver returns to an initialized state.

3. The crop growth monitoring method based on the multi-rotor unmanned aerial vehicle platform according to claim 2, wherein the data entering the data processing module through the wireless receiving module consists in that: data of the crop canopy reflectance spectra enters the data processing module through the wireless receiving module, and data of a sunlight incidence spectra enters the data processing module through an analog I/O interface.

4. The crop growth monitoring method based on the multi-rotor unmanned aerial vehicle platform according to claim 2, wherein the data are coupled into the crop growth monitoring model.

5. The crop growth monitoring method based on the multi-rotor unmanned aerial vehicle platform according to claim 1, wherein the data entering the data processing module through the wireless receiving module includes crop canopy reflectance spectra data entering the data processing module through the wireless receiving module, and sunlight incidence spectra data entering the data processing module through an analog I/O interface.

6. The crop growth monitoring method based on the multi-rotor unmanned aerial vehicle platform according to claim 5, wherein the data are coupled into the crop growth monitoring model.

7. The crop growth monitoring method based on the multi-rotor unmanned aerial vehicle platform according to claim 1, wherein the data are coupled into the crop growth monitoring model.

8. The crop growth monitoring method based on the multi-rotor unmanned aerial vehicle platform according to claim 1, wherein the length of the gimbal support is determined to be greater than a sum of the diameter of the air-flow velocity field at the canopy surface and a diameter of a viewing field of the multispectral crop growth sensor.

\* \* \* \* \*